*(12)* United States Patent
Olson (10) Patent No.: US 9,610,118 B2
(45) Date of Patent: Apr. 4, 2017

(54) METHOD AND APPARATUS FOR THE CANCELLATION OF MOTION ARTIFACTS IN MEDICAL INTERVENTIONAL NAVIGATION

(75) Inventor: Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1464 days.

(21) Appl. No.: 12/347,167

(22) Filed: Dec. 31, 2008

(65) Prior Publication Data

US 2010/0168558 A1 Jul. 1, 2010

(51) Int. Cl.
| | |
|---|---|
| *A61B 5/05* | (2006.01) |
| *A61B 5/0408* | (2006.01) |
| *A61B 5/042* | (2006.01) |
| *A61B 18/14* | (2006.01) |
| *A61B 5/06* | (2006.01) |
| *A61B 5/107* | (2006.01) |
| *A61B 5/00* | (2006.01) |
| *A61B 17/00* | (2006.01) |
| *A61B 34/20* | (2016.01) |

(52) U.S. Cl.
CPC ........ *A61B 18/1492* (2013.01); *A61B 5/0422* (2013.01); *A61B 5/062* (2013.01); *A61B 5/063* (2013.01); *A61B 5/1076* (2013.01); *A61B 5/6852* (2013.01); *A61B 34/20* (2016.02); *A61B 2017/00699* (2013.01); *A61B 2017/00703* (2013.01); *A61B 2034/2051* (2016.02); *A61B 2034/2063* (2016.02); *A61B 2034/2072* (2016.02)

(58) Field of Classification Search
CPC .............. A61B 5/05; A61B 2019/5263; A61B 2019/5251; A61B 2017/00703; A61B 2017/00699; A61B 2019/5272; A61B 18/1492; A61B 19/5244; A61B 5/6852; A61B 5/1076; A61B 5/063; A61B 5/062; A61B 5/0422; A61B 5/7207
USPC ................................................. 600/322, 310
See application file for complete search history.

(56) References Cited

U.S. PATENT DOCUMENTS 4,951,682 A * 8/1990 Petre ............................ 600/526
5,279,299 A   1/1994 Imran
(Continued)

FOREIGN PATENT DOCUMENTS

| EP | 1929956 | 6/2008 |
|---|---|---|
| EP | 2077526 | 7/2009 |

(Continued)

OTHER PUBLICATIONS

Orr, M. J. L., "Introduction to radial basis function networks", Apr. 1996 [retrieved on 2008-8-98. Retrieved from the internet: <URL: http://www.Ice. hut.fi/teachings/S-I 14.2001Orr_intro.ps. gz>.*
(Continued)

*Primary Examiner* — Katherine Fernandez
*Assistant Examiner* — Helene Bor
(74) *Attorney, Agent, or Firm* — Dykema Gossett PLLC (57) ABSTRACT

A method and apparatus for mapping a location of a point within the body is disclosed. A plurality of positional reference nodes are determined, each aligned on a first element. A second element is mapped with reference to the plurality of reference nodes to determine the relative location of a point on the second element.

21 Claims, 3 Drawing Sheets

(56) References Cited

U.S. PATENT DOCUMENTS

| | | | |
|---|---|---|---|
| 5,295,484 A | 3/1994 | Marcus | |
| 5,297,549 A | 3/1994 | Beatty | |
| 5,341,807 A | 8/1994 | Nardella | |
| 5,391,199 A * | 2/1995 | Ben-Haim | A61N 1/403 607/122 |
| 5,409,000 A | 4/1995 | Imran | |
| 5,447,529 A | 9/1995 | Marchlinski | |
| 5,462,545 A | 10/1995 | Wang et al. | |
| 5,546,940 A | 8/1996 | Panescu | |
| 5,546,951 A * | 8/1996 | Ben-Haim | 600/515 |
| 5,562,721 A | 10/1996 | Marchlinski | |
| 5,643,255 A | 7/1997 | Organ | |
| 5,662,108 A * | 9/1997 | Budd et al. | 600/374 |
| 5,673,704 A | 10/1997 | Marchlinski | |
| 5,702,386 A | 12/1997 | Stern et al. | |
| 5,713,946 A | 2/1998 | Ben-Haim | |
| 5,817,022 A | 10/1998 | Vesely | |
| 5,823,955 A | 10/1998 | Kuck | |
| 5,836,875 A | 11/1998 | Webster, Jr. | |
| 5,836,990 A | 11/1998 | Li | |
| 5,904,653 A | 5/1999 | Hatfield | |
| 5,921,923 A | 7/1999 | Kuck | |
| 5,944,712 A | 8/1999 | Frassica et al. | |
| 5,957,842 A | 9/1999 | Littmann | |
| 5,999,840 A | 12/1999 | Grimson et al. | |
| 6,091,995 A | 7/2000 | Ingle | |
| 6,139,498 A | 10/2000 | Katsman | |
| 6,200,314 B1 | 3/2001 | Sherman | |
| 6,216,027 B1 * | 4/2001 | Willis et al. | 600/424 |
| 6,235,018 B1 | 5/2001 | LePivert | |
| 6,289,239 B1 | 9/2001 | Panescu | |
| 6,304,776 B1 | 10/2001 | Muntermann | |
| 6,556,695 B1 | 4/2003 | Packer et al. | |
| 6,574,498 B1 * | 6/2003 | Gilboa | A61B 6/12 600/424 |
| 6,584,343 B1 * | 6/2003 | Ransbury et al. | 600/509 |
| 6,918,906 B2 | 7/2005 | Long et al. | |
| 7,263,397 B2 | 8/2007 | Hauck et al. | |
| 7,426,256 B2 * | 9/2008 | Rasche | A61B 6/5264 378/8 |
| 7,505,810 B2 | 3/2009 | Harley et al. | |
| 8,041,413 B2 | 10/2011 | Barbagli | |
| 8,213,693 B1 | 7/2012 | Li | |
| 8,611,983 B2 * | 12/2013 | Glossop | 600/424 |
| 2002/0151793 A1 | 10/2002 | Geiser et al. | |
| 2002/0188194 A1 | 12/2002 | Cosman | |
| 2003/0013958 A1 | 1/2003 | Govari et al. | |
| 2003/0063781 A1 * | 4/2003 | Philomin et al. | 382/118 |
| 2003/0065271 A1 | 4/2003 | Khoury | |
| 2003/0093067 A1 * | 5/2003 | Panescu | 606/32 |
| 2003/0130576 A1 | 7/2003 | Seeley | |
| 2003/0163176 A1 | 8/2003 | Bae | |
| 2003/0163178 A1 | 8/2003 | Davison | |
| 2004/0078036 A1 | 4/2004 | Keidar | |
| 2004/0097805 A1 | 5/2004 | Verard et al. | |
| 2004/0142485 A1 | 7/2004 | Flower | |
| 2004/0220471 A1 | 11/2004 | Schwartz | |
| 2004/0254437 A1 * | 12/2004 | Hauck et al. | 600/374 |
| 2005/0065434 A1 | 3/2005 | Bavaro et al. | |
| 2005/0203394 A1 | 9/2005 | Hauck | |
| 2005/0246130 A1 * | 11/2005 | Spicer et al. | 702/152 |
| 2007/0027392 A1 | 2/2007 | Schwartz | |
| 2007/0073179 A1 | 3/2007 | Afonso et al. | |
| 2007/0167801 A1 | 7/2007 | Webler et al. | |
| 2007/0255136 A1 | 11/2007 | Kristofferson et al. | |
| 2007/0299353 A1 | 12/2007 | Harlev | |
| 2008/0085043 A1 | 4/2008 | Watanabe et al. | |
| 2008/0137927 A1 | 6/2008 | Altmann et al. | |
| 2008/0177183 A1 | 7/2008 | Courtney | |
| 2008/0221425 A1 | 9/2008 | Olson et al. | |
| 2008/0221440 A1 | 9/2008 | Iddan | |
| 2008/0249395 A1 | 10/2008 | Shachar | |
| 2008/0287803 A1 | 11/2008 | Li et al. | |
| 2008/0300589 A1 | 12/2008 | Paul | |
| 2009/0107230 A1 | 4/2009 | Okcay | |
| 2009/0177089 A1 | 7/2009 | Govari et al. | |
| 2009/0264777 A1 | 10/2009 | Markowitz | |
| 2009/0275827 A1 | 11/2009 | Aiken | |
| 2009/0292206 A1 | 11/2009 | Sato | |
| 2009/0292209 A1 | 11/2009 | Hadjicostis | |
| 2010/0099991 A1 | 4/2010 | Snyder | |
| 2010/0165672 A1 | 7/2010 | Li | |
| 2010/0168569 A1 | 7/2010 | Sliwa | |
| 2010/0168572 A1 | 7/2010 | Sliwa | |
| 2010/0172554 A1 | 7/2010 | Kassab | |
| 2010/0312095 A1 | 12/2010 | Jenkins | |
| 2010/0312096 A1 | 12/2010 | Guttman | |
| 2011/0123088 A1 | 5/2011 | Sebok | |
| 2011/0125150 A1 | 5/2011 | Deno et al. | |
| 2011/0142316 A1 | 6/2011 | Wang | |
| 2011/0224655 A1 | 9/2011 | Asirvatham | |
| 2011/0230896 A1 | 9/2011 | Wallace | |
| 2011/0319765 A1 | 12/2011 | Gertner | |
| 2012/0095357 A1 | 4/2012 | Tran | |
| 2012/0158011 A1 | 6/2012 | Sandhu | |
| 2012/0165672 A1 | 6/2012 | Hill | |
| 2012/0172724 A1 | 7/2012 | Hill | |
| 2013/0226169 A1 | 8/2013 | Miller et al. | |
| 2013/0310674 A1 | 11/2013 | Decno | |

FOREIGN PATENT DOCUMENTS

| | | |
|---|---|---|
| JP | H10-33535 | 2/1998 |
| WO | WO-00/07501 | 2/2000 |
| WO | 2008/042423 | 4/2008 |

OTHER PUBLICATIONS

Chui, H., et al., "A new algorithm for non-rigid point matching" In IEEE Conference on Computer Vision and Pattern Recognition, 2002, vol. 2, ISBN: 0-7695-0662-3, pp. 44-51. [retrieved on 2008-8-9]. Retrieved from the internet: <URL: http://ieeexplore.ieee.org/xpl/>.*

Ju, T., et al., "Mean value coordinates for closed triangular meshes" in ACM Trans on Graphics, vol. 24(3), Jul. 2005, pp. 561-566 [Retrieved on 2008-8-91. Retrieved from the internet: <URL: http://faculty.cs.tamu.edu/schaefer/research/meanvalue.pdf>.*

Gepstein, Lior et al., "A novel method for nonfluoroscopic catheter-based electroanatomical mapping of the heart", Circulation 1997;95:1611-1622.

Wittkampf, Fred H. et al., "New Technique for Real-Time 3-Dimensional localization of regular intracardiac electrodes", Circulation—Journal of the American Heart Association Mar. 16, 1999, 1312-1317.

Casas, O.; "In Vivo and in Situ Ischemic Tissue Characterization Using Electrical Impedance Spectroscopy"; Annals New York Academy of Sciences, vol. 873; Reference pp. 51-58; Publication Date: Apr. 1999.

European Search Report in EP Application No. 09015744.7 (Jun. 4, 2010).

Author: Cho, Sungbo Title: Design of electrode array for impedance measurement of lesions in arteries Citation: Pysiol. Meas. 26 S19-S26 Publication Date: Mar. 29, 2005.

Author: Gales, Rosemary Title: Use of bioelectrical impedance analysis to assess body composition of seals Citation: Marine Mammal Science, vol. 10, Issue 1, Abstract Publication Date: Aug. 26, 2006.

Author: Masse, Stephane Title: A Three-dimensional display for cardiac activation mapping Citation: Pace. vol. 14 Publication Date: Apr. 1991.

Avitall, Boaz; "The Effects of Electrode-Tissue Contact on Radiofrequency Lesion Generation"; Pace, vol. 20; Reference pp. 2899-2910; Publication Date Dec. 1997.

Chakraborty, D. P.; "ROC curves predicted by a model of visual search"; Institute of Physics Publishing, Phys. Med. Biol. 51; Reference pp. 3463-3482; Publication Date: Jul. 6, 2006.

Dumas, John H.; "Myocardial electrical impedance as a predictor of the quality of RF-induced linear lesions"; Physiological Measurement, vol. 29; Reference Pages: Abstract only; Publication Date: Sep. 17, 2008.

(56) References Cited

OTHER PUBLICATIONS

Fenici, R. R,; "Biomagneticaiiy localizable multipurpose catheter and method for MCG guided intracardiac electrophysiology, biopsy and ablation of cardiac arrhythmias"; International Journal of Cardiac Imaging 7; Reference pp. 207-215; Publication Date: Sep. 1991.
Gao et al. "Computer-Assisted Quantitative Evaluation of Therapeutic Responses for Lymphoma Using Serial PET/CT Imaging", Academic Radiology, vol. 17. No. 4, Apr. 2010.
He, Ding Sheng; "Assessment of Myocardial Lesion Size during in Vitro Radio Frequency Catheter Ablation"; IEEE Transactions on Biomedical Engineering, vol. 50, No. 6; Reference pp. 768-776; Publication Date: Jun. 2003.
Himel, Herman D.; "Development of a metric to assess completeness of lesions produced by radiofrequency ablation in the heart"; Dept. of Biomedical Engineering, University of NC, Chapel Hill; Reference pp. i-xvii; 1-138; Publication Date: 2006.
Holmes, Douglas; "Tissue Sensing Technology Enhances Lesion Formation During Irrigated Catheter Ablation"; HRS; Reference Pages: Abstract only; Publication Date: 2008.
International Search Report and Written Opinion in PCT Application No. PCT/US2008/084194 (Feb. 5, 2009).
International Search Report and Written Opinion in PCT Application No. PCT/US2011/047235 (Dec. 14. 2011).
Supplementary European Search Report issued in EP Patent Application No. 11842330.0 (Jan. 20, 2014).
Title: International Search Report and Written Opinion of the International Searching Authority Citation: PCT/US2006/061714 Publication Date: Sep. 22, 2008.
Zheng, Xiangsheng, "Electrode Impedance: An Indicator of Electrode-Tissue Contact and Lesion Dimensions During Linear Ablation"; Journal of Interventional Cardiac Electrophysiology 4; Reference pp. 645-654; Publication Date: Dec. 2000.
Bar-Itzhack, Itzhack Y.; "New Method for Extracting the Ouaternion from a Rotation Matrix"; J. Guidance, vol. 23, No. 6, Engineering Notes; Reference pp. 1085-1087; Publication Date: Nov. 2000.
Cao, Hong, "FEM Analysis of Predicting Electrode Myocardium Contact from RF Cardiac Catheter Ablation System Impedance", IEEE Transactions on Biomedical Engineering, vol. 49, No. 6, Reference pp. 520-526, Publication Date: Jun. 2002.
Cao, Hong; "Using Electrical impedance to Predict Catheter-Endocardial Contact during RF Cardiac Ablation"; IEEE Transactions on Biomedical Engineering, vol. 49, No. 3; Reference pp. 247-253; Publication Date: Mar. 2002.
Chui, Haili; "A new algorithm for non-rigid point matching"; IEEE Conference on Computer Vision and pattern, vol. 2; Reference pp. 44-51; Publication Date: Jun. 2000.
Cinca, Juan; "Changes in Myocardial Electrical Impedance induced by Coronary Artery Occlusion in Pigs with and without Preconditioning"; Circulation; Publication Date: Nov. 1997.
del Rio; Carlos L.: "Early time course of myocardial electrical impedance during acute coronary artery occlusion in pigs, dogs, and humans"; Citation: Journal of Applied Physiology, vol. 99; Reference pp. 1576-1581, Publication Date: Jun. 15, 2005.
Fallert, MA; "Myocardial electrical impedance mapping of ischemic sheep hearts and healing aneurysms"; Citation: Circulation, vol. 87, No. 1; Reference pp. 199-207; Publication Date: Jan. 1993.
Fitzpatrick; Michael J; "Handbook of medical imaging vol. 2. Medical image processing and analysis" SPIE—The international society for optical engineering; Reference pp. 451-514; Publication Date: Jun. 2000.
Haines, DE; "Observations on electrode-tissue interface temperature and effect on electrical impedance during radiofrequency ablation of ventricular myocardium"; Circulation, vol. 82, No. 3; Reference pp. 1034-1038; Publication Date: Sep. 1990.
Hoffmann, Ellen; "Biophysical parameters of radiofrequency catheter ablation"; Citation: International Journal of Cardiology; vol. 37; Reference pp. 213-222; Publication Date: Dec. 1992.
Hom, Berthold K.P.; "Closed-form solution of absolute orientation using unit quaternions"; Journal of teh Optical Society of America, vol. 4; Reference pp. 629-642; Publication Date: Apr. 1987.
Howie, Michael B.; "An Evaluation of a New Two-Electrode Myocardial Electrical Impedance Monitor for Detecting Myocardial Ischemia"; Anesth. Analg, vol. 92:12-6; Reference pp. 12-16; Publication Date: Jan. 2001.
International Search Report and Written Opinion in PCT Application No. PCT/US2011/063591 (Apr. 16, 2012).
Kearsley; Simon; "On the orthogonal transformation used for structural comparisons"; Acta Crystallographica Vo. A45; Reference pp. 208-210; Publication Date: Feb. 1989.
Ko, Wen-Chin; "New Method for Predicting Efficiency of Heating by Measuring Bioimpedance During Radiofrequency Catheter Ablation in Humans"; Journal of Cardiovascular Electrophysiology, vol. 12, No. 7; Reference pp. 819-823; Publication Date: Jul. 2001.
Lang, Christopher C.E.; "Endocardial impedance mapping during circumferential pulmonary vein ablation of atrial fibrillation differentiates between atrial end venous tissue"; Heart Rhythm Society, vol. 3, No. 2; Reference pp. 171-178; Publication Date: Feb. 2006.
Ragheb, T.; "The Impedance of a Spherical Monopolar Electrode"; Annals of Biomedical Engineering, vol. 20; Reference pp. 617-627; Publication Date: Nov. 1992.
Ragheb, T.; "The Polarization Impedance of Common Electrode Metals Operated at Low Current Density"; Annals of Biomedical Engineering, vol. 19, Issue 2; Reference pp. 151-163, Publication Date: Mar. 1991.
Salazar, Yolocuauhtli; "Effect of electrode locations and respiration in the characterizaiton of myocardial tissue using a transcatheter impedance method"; Physiological Measurement, No. 25; Reference pp. 1095-1103, Publication Date: Oct. 2004.
Salazar, Yolocuauhtli: "Transmural Versus Nontransmural in Situ Electrical Impedance Spectrum for Healthy, Ischemic, and Healed Myocardium"; IEEE Transactions on Biomedical Engineering, vol. 51 No. 8; Reference pp. 1421-1427; Publication Date: Aug. 2004.
Schwartzman, David; "Electrical Impedance Properties of Normal and Chronically Infarcted Left Ventricular Myocardium"; Journal of Interventional Cardiac Electrophysiology, vol. 3; Reference pp. 213-224; Publication Date: Oct. 1999.
Strickberger, S. Adam; "Relation between impedance and endocardial contact during radiofrequency catheter ablation"; American Heart Journal, vol. 1298, No. 2; Reference pp. 226-229: Publication Date: Aug. 1994.
Title: 3D Slicer Citation: 3D Slicer "Modules Fiducials—Documentation—3.2" (2008).
Wolf, Tamir; "Three-dimensional endocardial impedance mapping: a new approach for myocardial infarction assessment"; AJP—Heart and Circulatory Physiology, vol. 280; Reference pp. 179-188; Publication Date: Jan. 2001.
Chan, R.C. et al., "Intraprocedural fusion of electroanatomical maps (EAM) with imaging data based on rapidly-sampled volumetric point clouds from continuous EAM catheter tracking", Proceedings of SPIE, vol. 6509, Mar. 6, 2007.
Packer, Douglas L. et al., "New generation of elctro-anatomic mapping: full intracardiac ultrasound image integration", Europace, vol. 10, No. Supplement 3, Nov. 1, 2008.
Supplementary European Search Report in EP Application No. 11850605.4 (Feb. 25, 2015).

* cited by examiner

METHOD AND APPARATUS FOR THE CANCELLATION OF MOTION ARTIFACTS IN MEDICAL INTERVENTIONAL NAVIGATION

BACKGROUND OF THE INVENTION a. Field of the Invention

The present invention relates to a method and apparatus for mapping the location of a point within a body. More specifically, the present invention relates to a method and apparatus for mapping the location of a node, such as a distal end electrode of a catheter, disposed within a body and located at a point, which is desired to be tracked, through reference to a plurality of reference nodes, such as a plurality of electrodes disposed within a reference catheter, and interpolation between the node and the plurality of reference nodes. Further, the present invention, upon mapping, will filter out any motion artifacts which may distort the location and/or movement of the node.

b. Background Art

It is well-known that an element, or node, of a medical device may be tracked within the body of a patient by measuring electrical signals passing through tissues, as well as other anatomic structures, in the body, through a navigational system (sometimes called a location mapping system). The location of the node may also be tracked by other means, such as magnetic and ultrasound tracking means. As an example, intersecting electromagnetic fields may be utilized to track the location of one or more elements, such as one or more catheter tips (or, more accurately, one or more electrodes disposed on a plurality of catheters), which may be placed at a point within a body. Further, the addition of a reference node at a known, fixed location may be employed to determine the location, in relation to the reference node and other parts of a patient's anatomy, of the node, or element, which corresponds to the location of a point within the body.

Systems for tracking medical elements within a body are disclosed in various U.S. patents. For example, U.S. Pat. No. 5,297,549, entitled "Endocardial Mapping System," issued on 29 Mar. 1994 discloses a mapping system utilizing an array of electrodes placed in a heart. In this reference, the shape of the chamber, and the location of the electrodes, are determined via impedance plethysmography. Further, electrical measurements taken from the electrode array and referenced to a surface contacting electrode are used to generate a three-dimensional map of electrical activity. In another embodiment, a two-dimensional map of the electrical activity within the endocardial surface is computed.

Additionally, U.S. Pat. No. 5,311,866, entitled "Heart Mapping Catheter," issued on 17 May 1994, discloses a mapping catheter assembly. In this reference, a lumen is provided to accept a catheter which includes a distal tip electrode assembly. In operation, an array of electrode sites are deformed into a spherical shape after the assembly is placed in a heart chamber. A reference electrode assembly is advanced into contact with the heart wall to provide calibration information for the array.

For another example, U.S. Pat. No. 5,553,611, entitled "Endocardial Measurement Method," issued on 10 Sep. 1996, discloses a method for taking a collection of measurements from a set of measurement electrodes in an effort to determine the position of a catheter in a heart chamber.

Further, U.S. Pat. No. 5,662,108, entitled "Electrophysiology Mapping System," issued on 2 Sep. 1997, discloses a mapping catheter positioned in a heart chamber, in which active electrode sites are activated to impose an electric field within the chamber. The blood volume and wall motion modulates the electric field, which is detected by passive electrode sites on the preferred catheter. In the reference, electrophysiology measurements, as well as geometry measurements, can be taken from the passive electrodes and used to display a map of intrinsic heart activity.

Additionally, U.S. Pat. No. 5,697,377 (and its progeny), entitled "Catheter Mapping System And Method," issued on 16 Dec. 1997, discloses a system and method for catheter location mapping. Three substantially orthogonal alternating signals are applied through the patient, directed substantially toward the area of interest to be mapped. A catheter, equipped with at least a measuring electrode for cardiac procedures, is positioned at various locations either against the patient's heart wall, or within a coronary vein or artery. A voltage is sensed between the catheter tip and a reference electrode, preferably a surface electrode on the patient, which voltage signal has components corresponding to the three orthogonal applied current signals. U.S. Pat. No. 5,983,126, entitled "Catheter Location System And Method," issued on 9 Nov. 1999, is a continuation of this reference.

Further, U.S. Pat. No. 6,049,622, entitled "Graphic Navigational Guides For Accurate Image Orientation And Navigation," issued on 11 Apr. 2000, and discloses a method for the acquisition of image data having an attached spatial coordinate system. A navigational guide can then employ the coordinate system to indicate the orientation of the imaged object and the location of the viewer with respect to the imaged object.

Additionally, U.S. Pat. No. 6,240,307, entitled "Endocardial Mapping System" (and its progeny) issued on 29 May 2001, discloses a system for mapping the electrical activity of a heart. The system includes a set of electrodes spaced from the heart wall and a set of electrodes in contact with the heart wall. Voltage measurements from the electrodes are used to generate three-dimensional and two-dimensional maps of the electrical activity of the heart. U.S. Pat. Nos. 6,603,996; 6,647,617; 6,826,420 and 6,826,421 are divisionals of this reference. Further, U.S. Pat. Nos. 6,640,119; 6,728,562 and 6,990,370 are derivatives of this reference.

Finally, U.S. Pat. No. 6,556,695, entitled "Method For Producing High Resolution Real-Time Images, Of Structure And Function During Medical Procedures," issued on 29 Apr. 2003, discloses the acquisition of the images of a heart with a high resolution medical imaging system used to construct a dynamic high resolution 4D model.

The contents of each of the above-cited references (including their progenies as named herein) are herein incorporated by reference in their entireties.

One difficulty in conventional location mapping systems and techniques concerns the real and imaginary movements that such tracking instruments routinely detect and, more specifically, the difficulty in discerning between the two types of movements. "Real movements" are actual, physical movements caused by the motion of a patient's body as a whole, or by parts of the body in relation to one another. For example, respiration causes expansion of the chest and consequent displacement of the organs contained within the chest cavity, including the heart. Additionally, "imaginary" movements may further add to the motion created by the physical movements described herein. For example, respiration may also alter the electrical impedance distribution of the body by the introduction of air into the chest cavity. The variations in the electrical field may result in readings that suggest additional motion by the node. For purposes of the present invention, these real and imaginary movements are collectively referred to as "motion artifacts."

Interventional navigational systems are used to map points within the body. These systems use electromagnetic mapping algorithms in conjunction with an image or model of the anatomical environment in which the tracked node (i.e., the node whose location is to be tracked) operates. Such images are often derived from external imaging equipment currently known in the art, such as computed topography ("CT") and magnetic resonance imaging ("MRI") equipment.

Often, the result is a surface model that may be interpolated from points in three dimensions ("3D") collected from an internal tracking node. However, because such surface models are often static, the motion artifacts described above may be confusing and distracting to an operator, may affect the accuracy of the tracking, and, consequently, may negatively impact treatment quality.

Because therapies and procedures using such tracking systems are often exceedingly delicate, such motion artifacts are undesirable. Thus, a system that reduces or minimizes such motion artifacts would enhance the quality of care provided. Consequently, it would be advantageous to be able to eliminate, or substantially eliminate, both real and imaginary movement in a navigational mapping system.

BRIEF SUMMARY OF THE INVENTION

It is desirable to be able to control motion artifacts created in a three-dimensional internal medical navigational device to overcome the above-stated disadvantages. The present invention provides a method and apparatus of medical interventional navigation systems which reduces motion artifacts that currently exist in present navigational devices.

In an embodiment, a plurality of reference nodes are aligned at known points within a body. The location of a further node, distinct from the plurality of reference nodes, is determined relative to each of the plurality of reference nodes.

The foregoing and other aspects, features, details, utilities, and advantages of the present invention will be apparent from reading the following description and claims, and from reviewing the accompanying drawings.

DETAILED DESCRIPTION OF THE INVENTION

Medical interventional navigation systems provide the ability to track the position of catheters, surgical tools and other devices inside a body. These systems typically use magnetic, electric, ultrasound or other radiation or energy sources or tracking means to determine the x, y and z coordinates of the devices within the body. When these devices are placed inside moving organs, such as the heart, the effect of any movement, or force, of those organs on the devices will most likely cause the devices to move. This effect is referred to herein as real movement, and can be illustrated in a respiration example, where the movement of the chest cavity will cause the movement of any organ contained within the chest cavity.

Additionally, these systems may also detect and report imaginary movement of the devices due to changes in the navigation field. For instance, in an impedance-based system, respiration of the body will alter the system conductance of the thorax, which will, in turn, alter the sensed electrical potential at the tracked device (i.e., the device whose location is to be tracked). Because the system assumes that the navigation field is static, this change in sensed electrical potential will be perceived by the system as movement of the tracked device. In other words, although the tracked device may be completely stationary, the system will report that the tracked device is moving.

To this end, the present invention provides a medical interventional navigation system that eliminates, or at least substantially reduces, both types of the aforementioned movements, or motion artifacts. Thus, the present invention acts to provide virtual stabilization of the tracked device, in which the appearance of stability of the tracked device is provided to a user of the medical interventional navigation system while the heart, for example, continues to beat and, consequently, move.

Oftentimes, such systems are used in conjunction with an image or model of the anatomical environment in which the tracked device operates. Further, such images are often derived from currently-known external imaging equipment, such as CT or MRI equipment. Additionally, such systems may have the ability to "collect," or define, a geometry by moving the tracked device throughout a region desired to be mapped, and recording all the points the tracked device, which can be called a "mapping" device, has visited. This collection of points is often referred to as a cloud of points. In this way, a surface model can be subsequently "wrapped" around the collected points to provide a backdrop or context for the tracked device when the location thereof is displayed on a computer screen.

One system exemplary of such a medical interventional navigation system is the ENSITE™ NAVX™ system integrated into the ENSITE™ Advanced Mapping System by St. Jude Medical, Atrial Fibrillation Division, Inc., of Minnetonka, Minn. The ENSITE™ NAVX™ system provides non-fluoroscopic navigation of both specialized and conventional electrophysiology catheters. The navigation methodology used therein is based on the principle that when an electric current is applied across a pair of cutaneous electrodes, a voltage gradient is created along the axis between the pair of cutaneous electrodes. While any number of surface electrode pairs may be used, typically, six (6) cutaneous electrodes (combining to comprise three (3) surface electrode pairs) are placed on the body of the patient: anterior to posterior (i.e., the z-axis), left to right lateral (i.e., the y-axis) and superior (neck) to inferior (left leg) (i.e., the x-axis). These three (3) electrode pairs thus form three (3) orthogonal axes, with the patient's heart oriented near the intersection of all three (3) orthogonal axes.

Figure 1:
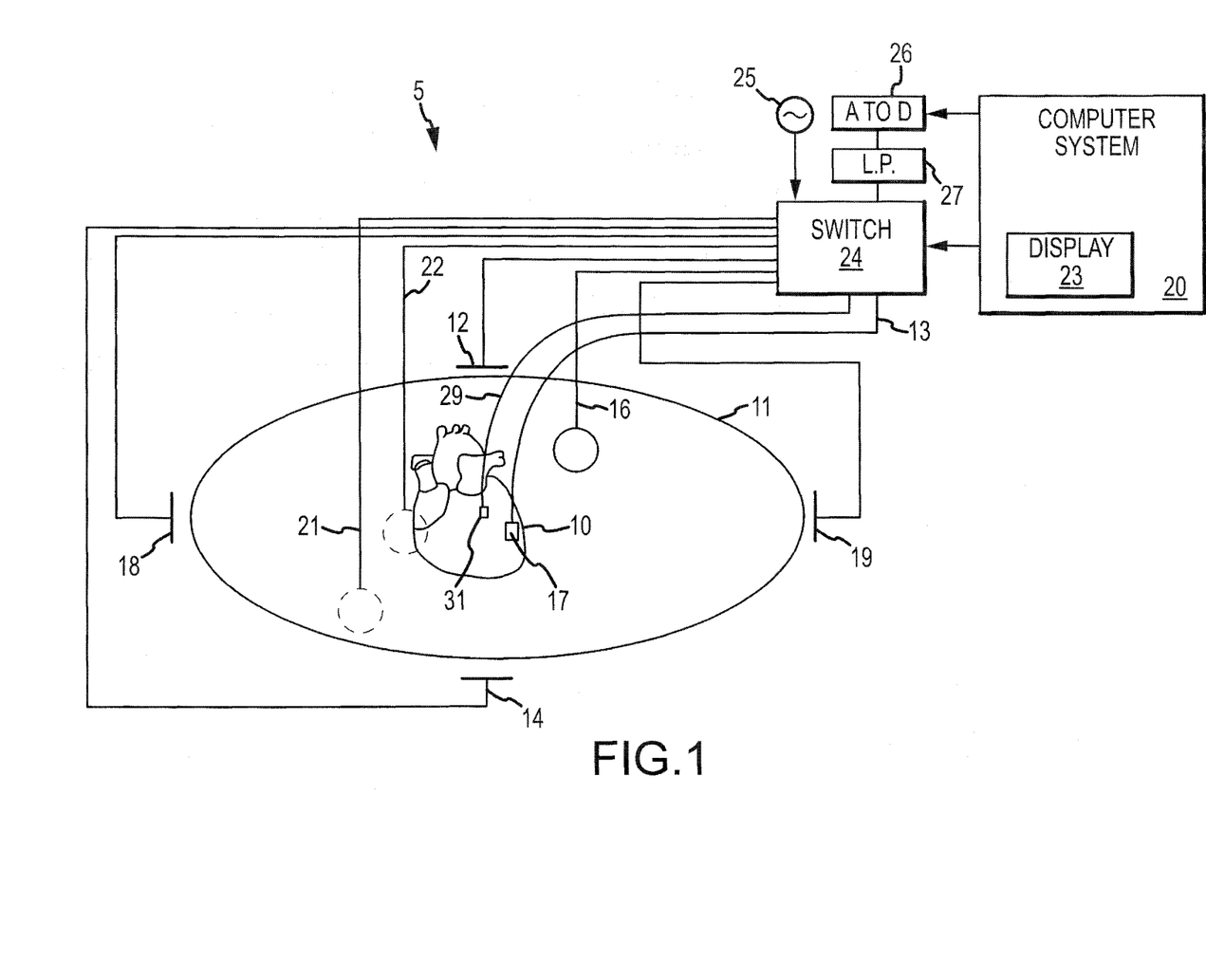
FIG. 1 is a schematic representation of one embodiment of a medical interventional navigation system.

FIG. 1 illustrates an exemplary embodiment of medical navigational system 5. Medical navigational system 5 will be briefly addressed herein, as it is one such system that may utilize the mapping techniques addressed in detail herein. Medical navigational system 5 is also discussed in detail in U.S. Pat. No. 7,263,397, which issued on 28 Aug. 2007. The entire disclosure of U.S. Pat. No. 7,263,397, which is entitled "Method And Apparatus For Catheter Navigation And Location And Mapping In The Heart," is incorporated by reference herein in its entirety.

Referring to FIG. 1, in which patient 11 is depicted as an oval for clarity, three (3) sets of surface electrodes (as described herein) are illustrated as 18, 19 along the y-axis; 12, 14 along the x-axis; and 16, 22 along the z-axis. The assignment of the x, y, z axis to a particular direction is arbitrary and should not be construed to be limiting the invention. A further surface electrode 21, that acts as an electrical reference, which may be referred to as "belly" electrode 21, is also illustrated in FIG. 1. Each surface electrode 12, 14, 16, 18, 19, 22 is independently coupled to multiplex switch 24. Heart 10 of patient 11 lies between the various pairs of surface electrodes 12, 14, 16, 18, 19, 22. Also illustrated in FIG. 1 is catheter 13, illustrating as including distal electrode 17 (again, for clarity). Multiple electrodes on catheter 13 may be used. Reference electrode 31, which is preferably in a fixed location, such as attached to heart 10, is also illustrated in FIG. 1 as being disposed on a distal end of reference catheter 29. For calibration purposes, reference electrode 31 is known to be stationary on heart 10, and, further, is known to be in a known position on heart 10.

Any pair of surface electrodes 12, 14, 16, 18, 19, 22 may be selected for excitation by software running on computer system 20, which couples each surface electrode 12, 14, 16, 18, 19, 22 to signal generator 25. One pair of surface electrodes, for example, surface electrodes 18, 19, may be excited by signal generator 25 as that pair, in turn, generates an electric field in the body of patient 11 and, more accurately, in heart 10. During the delivery of a current pulse, remaining surface electrodes 12, 14, 16, 22 are preferably referenced to "belly" surface electrode 21, and the voltages impressed on remaining surface electrodes 12, 14, 16, 22 can be measured by analog-to-digital converter 26. Suitable low pass filtering of the digital data may be subsequently performed to remove electronic noise, for example, after suitable low pass filtering in filter 27. In this manner, various patch electrodes 12, 14, 16, 18, 19, 22 can be divided into driven and non-driven surface electrode pairs. While one pair of surface electrodes are driven by signal generator 25, the remaining non-driven surface electrodes can be used as references to synthesize the orthogonal axes, described above.

In this way, surface electrodes, such as those discussed herein, may be connected to mapping systems such as the ENSITE™ Advanced Mapping System described above, which sends an electrical signal through each pair of surface electrodes 12, 14, 16, 18, 19, 22 to create a voltage gradient along each orthogonal axis, forming a transthoracic electrical field. Conventional electrophysiology catheters (e.g., representative catheter 13) may be connected to the ENSITE™ Advanced Mapping System, described herein, and advanced to heart 10. As representative catheter 13 enters the transthoracic electrical field, an electrode disposed thereon (e.g., distal electrode 17) senses voltage, which is preferably timed to the creation of the gradient along each orthogonal axis. Using the sensed voltages as compared to the voltage gradient on all three orthogonal axes, ENSITE™ NAVX™ can then calculate the three-dimensional position of each electrode 17 on representative catheter 13.

Figure 2:
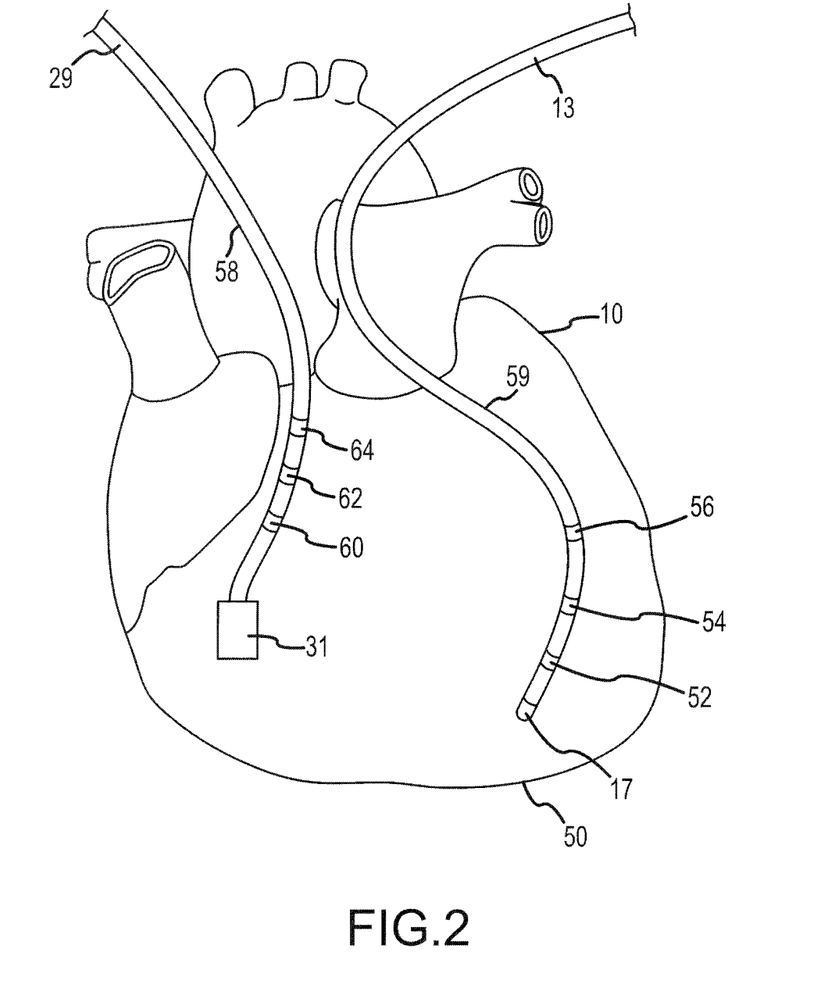
FIG. 2 is a schematic of a catheter in a heart chamber.

For further illustration, FIG. 2 illustrates representative catheter 13 disposed in heart 10. In FIG. 2, catheter 13 is illustrated as being located in left ventricle 50. Catheter 13 is further illustrated as having additional electrodes 52, 54, 56. Since these electrodes lie in heart 10, the location process detects their location in heart. Additionally illustrated in FIG. 2 is independent catheter 29, which is illustrated as having independent electrode 31.

Referring to FIG. 1, the ENSITE™ Advanced Mapping System further comprises display 23 for displaying, in real-time, the location of electrodes 17, 52, 54, 56, as well as catheter 13. By tracking the position of catheter 13, ENSITE™ NAVX™ provides non-fluoroscopic navigation, mapping and creation of chamber models that are detailed and have accurate geometries. In the latter regard, a physician may sweep catheter 13 across heart 10 to outline the structures by relaying signals to computer system 20, which then generates a three-dimensional model of heart 10. This model may be utilized for any appropriate purpose, such as assisting a physician in guiding an ablation catheter to a heart treatment location, cardiac mapping, etc.

As these surface models are typically static, the effect of the aforementioned motion artifacts can be confusing to medical interventional navigation system 5. For example, in endocardial catheter navigation, although catheter 13 may be in a stationary position relative to the endocardial tissue, it may appear to be moving with respect to the static surface model. During ablation therapy, the operator desires to place the tip of catheter 13 on the endocardium to create a lesion, facilitating the delivery of radio frequency (RF) energy or radiation. It is imperative, in this example, then, that catheter 13 remain stable during this process, as any motion of catheter 13 relative to the static surface model may call into question whether catheter 13 is actually stable.

Therefore, to map the position of a device pursuant to the present invention, a mapping function may be defined as:

$$f: \Re^3 \Rightarrow \Re^3$$

such that the mapping goes from the raw, unstabilized coordinates to stabilized coordinates, then providing a method to eliminate motion artifacts can be equated to solving the above mapping function. The mapping function can further be defined by finding the transformation that takes the current position of each electrode 17, 52, 54, 56 on catheter 13 and compares it with a set of constant positions, such as those set forth by catheter 29, which includes electrode 31.

For example, in the case where there are ten (10) electrodes, each of those electrodes can be used to generate input/output samples from which to solve the mapping function. The current observed position of the electrode represents the input and the initialized constant position represents the output.

$$\{x_i, y_i\}_{i=1,N}$$

Typical assumptions that mapping should be continuous and smooth are assumed. The constant positions can be arbitrarily defined in numerous fashions.

Referring again to FIG. 2, the present invention utilizes reference catheter 29. Reference catheter 29 comprises main shaft 58, having a proximal end and a distal end, through which leads may pass to various electrodes. Reference catheter 29 comprises reference electrode, or reference node, 31, provided at or near the distal end of reference catheter 29. Preferably, reference node 31 may be an electrode capable of detecting and measuring fluctuations in an electromagnetic field. Additional to reference node 31, reference catheter 29 may be provided with a plurality of other reference nodes 60, 62, 64 dispersed along its length. Similar to reference node 31, other reference nodes 60, 62, 64 may also be electrodes capable of detecting and measuring electromagnetic fields. Reference catheter 29 may be any type of catheter with electrodes. For example and without limitation, reference catheter 29 may comprise a mapping catheter, an intracardiac echocardiography ("ICE") catheter, and/or a pacemaker (e.g., a pacemaker with at least one electrode linked to the ENSITE™ NAVX™ system).

In operation, surface electrodes 12, 14, 16, 18, 19, 22 may be applied externally to the body, in the manner described above. Preferably, surface electrodes 12, 14, 16, 18, 19, 22 are used to create three (3) orthogonal potential fields. Reference nodes 31, 60, 62, 64 of reference catheter 29 measure the electrical potential at the location of the electrode which has been imposed by the cutaneous electrodes which have been modulated by the various body tissues to map the location of reference catheter 29 with respect to all three orthogonal axes, and therefore the location of reference catheter 29 in heart 10. A second, measuring catheter 13 likewise may measure its own position by measuring the same electromagnetic fields using reference catheter 29 and reference nodes 31, 60, 62, 64.

In one embodiment, reference catheter 29 is placed in a fixed, known location (or alternately, a location that can be substantially definitively ascertained). For example, reference catheter 29 may be placed in the coronary sinus, where it is unlikely to shift, and can provide a good reference point relative to heart 10. Although the coronary sinus is mentioned in detail as one location for reference catheter 29, reference catheter 29 may be placed anywhere in the heart so long as its location is fixed. Software resident on computer system 20 can receive the inputs of both reference catheter 29 and catheter 13, and may then interpolate a more precise location of catheter 13 within the body. If the method and apparatus of the present invention are used to map locations of catheter 13 relative to heart 10, then because reference nodes 31, 60, 62, 64 of reference catheter 29 occupy a series of locations in three dimensions with respect to heart 10, the motion of reference nodes 31, 60, 62, 64 will be complementary to the movement of heart 10 due to beating, respiration and other phenomena, i.e., the motion artifacts. Therefore, if the locations of reference nodes 31, 60, 62, 64 are defined to be fixed, then motion artifacts may be eliminated between measuring electrode 17 and heart 10.

In operation, reference catheter 29 may be placed in the vicinity of the working environment, which in the example herein, means within the vicinity of heart 10. The position of reference catheter 29 may be tracked and, after its location has been definitively ascertained, the motion of any other catheters in the working environment may also be determined, relative to the position of reference catheter 29. The position of reference catheter 29 is defined to be stationary, and has the effect of negating any motion artifacts of other catheters in the vicinity when those motion artifacts are negligible with respect to the actual movement of reference catheter 29. As the separation between reference catheter 29 and any tracked catheter element increases, the effects of the motion artifacts, described above, may likewise increase.

Various methodologies may be used to define a constant position of reference catheter 29. If the motion of reference catheter 29 is sampled over time, the mean position of reference catheter 29, and more specifically the nodes 31, 60, 62, 64 on reference catheter 29, could be used as the constant position. Alternatively, when used to map points near and within heart 10, a point could be taken at a specific cardiac phase, such as an end diastole. The mapping could then be defined such that a different constant position is chosen for each point in time in the cardiac phase of the heart. Alternatively a secondary or external location system may be employed to define the constant reference location. For example, a primary system that employs electrical impedance as its navigation system may use a magnetic location system to provide the constant reference location.

As described herein, the present invention utilizes a plurality of nodes or electrodes 31, 60, 62, 64 resident on reference catheter 29 to enhance the location accuracy and mapping, and to correct for defects inherent in using only one measuring catheter. The various inputs from the multiple electrodes 31, 60, 62, 64 may be utilized to create a static model of the location of reference catheter 29 in the body or with respect to a particular organ, such as heart 10. The use of multiple nodes defines a broader fixed location, and a wider frame of motion in which a tracked catheter may operate without increased motion artifacts. Each of the multiple nodes comprising the multi-point reference system of the present invention are impedance-based nodes, magnetic-based nodes, or optical-based nodes. Accordingly, all of the nodes making up the multi-point reference system of the present invention may be of the same type. The present invention is an extension to the use of a single node or electrode as a position reference which is common in current utilization of such systems. A single positional reference has the capability of eliminating only translation of the reference frame, whereas the present invention has the potential to eliminate higher order changes in the reference frame such as rotation, scale, and most generally deformations.

One method of creating a static model of heart 10 from the inputs received from electrodes 31, 60, 62, 64 on reference catheter 29 may be to use a thin-plate splines algorithm. The thin-plate splines algorithm is a method of interpolation between a set of control points. The thin-plate splines algorithm minimizes a factor analogous to the bending energy of a thin metal plate which is forced to pass through the reference points. In one embodiment, the thin-plate splines algorithm is the sum of a set of weighted basis functions centered at each reference point, where the basis function is typically:

$$r^2 \log r^2$$

where r is the radial distance of an input point from the particular basis function center. A regularization parameter $\lambda$ may be introduced into the linear algebraic equations to determine the thin-plate splines solution to create a smoother solution. If a regularization parameter is used in this context, the control points would not pass through the constant reference positions perfectly and therefore would not stabilize the model space entirely. This would represent a tradeoff of stabilization of the model versus a more robust solution that would be less sensitive to such things as random or other position errors that may be impressed on the location data of the reference catheter.

Also, in one embodiment, radial basis function networks may be utilized to perform mapping functions to map the position of reference catheter 29 to a fixed position relative to heart 10 or other elements of the body. A radial basis network function of the form:

$$y = f(x) \equiv \sum_{i=0}^{L} h_i \kappa\left(\frac{(x - c_i)}{w_i}\right)$$

(where $\kappa$ is the Gaussian-shaped basis function) is employed in this embodiment.

Using these formulations, undesirable motion artifacts may be minimized by mapping the position of a fixed catheter or catheters to a fixed position. The location of all the catheters being tracked (both stationary and non-stationary) are processed with the computed mapping transformation, thus stabilizing the model reference frame. Although these transformations may require computation at each time point, modern computer hardware is sufficient to realize the computational load, which may be reduced by sampling fewer reference nodes on reference catheter 29. The computational load may also be reduced by reducing the frequency at which the mapping function is computed. The previously computed mapping function may be used if the catheter electrodes have not moved significantly from their previous location.

It should be noted that the mapping methods and functions described herein are illustrative, and are not intended to limit the scope of the present invention. Rather, any method of function regression which may be used to determine a mapping function from a set of samples is disclosed by the present invention.

Figure 3:
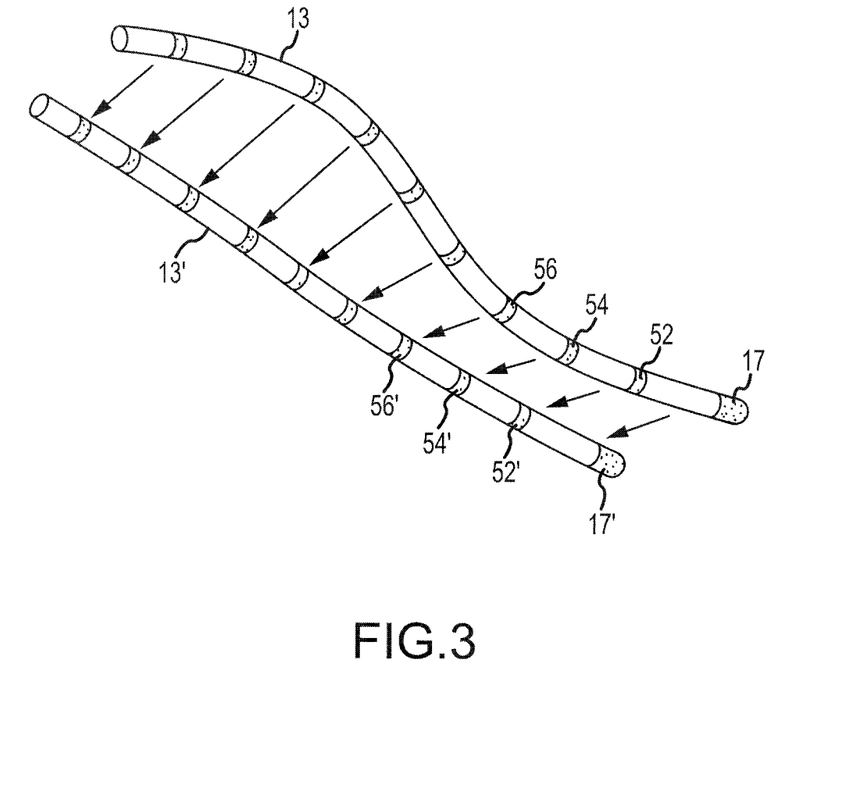
FIG. 3 illustrates an exemplary mapping of a catheter, in accordance with the present invention.

FIG. 3 illustrates an exemplary illustration of the mapping of catheter 13, as illustrated in actual position with heart 10, to static position, referenced as 13', when employing the thin splines algorithm described herein. Static position 13' may, for example, be displayed on display 23 of computer system 20. Further, static position 13' may include static positions of each electrode present on catheter 13. The static position of each electrode is referenced as the reference number of each electrode primed. When the mapping technique, as described herein, is applied to catheter 13, static position 13' results, allowing a physician to see the location of catheter 13 without the effect of the motion artifacts.

Although embodiments of the invention have been described above with a certain degree of particularity, those skilled in the art could make numerous alterations to the disclosed embodiments without departing from the scope of the invention. For example, a feature of the invention is the definition of reference catheter 10 to occupy a known location. Although the coronary sinus is disclosed as a location, other locations may also be suitable. A high right atrium catheter and a right ventricle lead could replace or supplement electrode points in the coronary sinus and provide reference points which span more of the volume and dimensions of the heart.

All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation or use of the invention. Joinder references (e.g., attached, coupled, connected and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for determining a motion compensated node location in a three-dimensional coordinate system associated with a node disposed on a first medical device within a body, the method comprising:
   determining a plurality of reference locations in said coordinate system corresponding to a positional reference node within the body and corresponding to a plurality of secondary reference nodes relative to the positional reference node, wherein the positional reference node and each of the secondary reference nodes are disposed on a second medical device;
   determining a mapping transformation function configured to transform, for the positional reference node and each of the plurality of secondary reference nodes, the respective determined reference locations to be defined as corresponding constant locations over time in said coordinate system such that the reference locations are an input to the mapping transformation function and the corresponding constant are an output to the mapping function to thereby define a static model of the second medical device, wherein the transformed reference locations of the corresponding constant locations define a static position of the second medical device; and
   determining the motion compensated node location associated with the node disposed on the first medical device by
      applying the determined mapping transformation function to a raw node location in said coordinate system associated with the node, wherein the node disposed on the first medical device comprises a first node and wherein the first medical device further comprises a second node, the first node and the second node selected from at least one of an electromagnetic field node and a magnetic position node, wherein applying the determined mapping transformation to the raw mode location includes:
   applying the determined mapping transformation function to a first raw node location associated with the first node to determine a first motion compensated node location associated with the first node; and
   applying the determined mapping transformation to a second node location associated with the second node to determine a second motion compensated node location associated with the second node.

2. The method of claim 1, wherein the reference locations corresponding to both the positional reference node and secondary reference nodes are determined through measuring at least one potential gradient passing through the body.

3. The method of claim 1, wherein at least one of the reference locations corresponding to at least one of the positional reference node and secondary reference nodes is determined through magnetic means.

4. The method of claim 1, wherein at least one of the reference locations corresponding to at least one of the positional reference node and secondary reference nodes is determined through ultrasound means.

5. The method of claim 1, wherein at least one of the reference locations corresponding to at least one of the positional reference node and secondary reference nodes is determined through electrical impedance means.

6. The method of claim 1, wherein a thin plate splines algorithm is used to determine the mapping transformation function.

7. The method of claim 1, wherein a radial basis function network is used to determine the mapping transformation function.

8. The method of claim 1, wherein the mapping transformation function is generated using a mean position of the positional reference node and each of the plurality of secondary reference nodes.

9. The method of claim 1, wherein the mapping transformation function is generated at a specific cardiac phase.

10. A method for determining a motion compensated node location in a three-dimensional coordinate system associated with a node disposed on a first medical device with a body, the method comprising:

determining a plurality of reference locations in said coordinate system corresponding to a plurality of reference nodes disposed on a second medical device;

determining a mapping transformation function configured to transform the reference locations associated with each of the plurality of reference nodes to be defined as corresponding constant locations over time in said coordinate system such that the reference locations are an input to the mapping transformation function and the corresponding constant locations are an output to the mapping transformation function to thereby define a static model of the second medical device, wherein the transformed reference locations of the corresponding constant locations define a static position of the second medical device; and determining the motion compensated node location associated with the node disposed on the first medical device by:

applying the determined mapping transformation function to a raw node location in said coordinate system associated with the node, wherein the node disposed on the first medical device comprises a first node and wherein the first medical further comprises a second node, the first node and the second node selected from at least one of an electromagnetic field node and a magnetic position node, wherein applying the determined mapping transformation to the raw node location includes:

applying the determined mapping transformation function to a first raw node location associated with the first node to determine a first motion compensated node location associated with the first node; and applying the determined mapping transformation function to a second raw node location associated with the second node to determine a second motion compensated node location associated with the second node.

11. The method of claim 10, wherein the reference nodes are electrodes.

12. The method of claim 10, where determining the plurality of reference locations corresponding to the plurality of reference nodes comprises measuring the voltage at a point in a potential gradient between a pair of electrodes.

13. The method of claim 10, where determining the plurality of reference locations corresponding to the plurality of reference nodes is determined through magnetic means.

14. The method of claim 10, where determining the plurality of reference locations corresponding to the plurality of reference nodes is determined through ultrasound means.

15. The method of claim 10, where determining the plurality of reference locations corresponding to the plurality of reference nodes is determined through electrical impedance means.

16. The method of claim 10, wherein a thin plate splines algorithm is used to determine the mapping transformation function.

17. The method of claim 10, wherein a radial basis function network is used to determine the mapping transformation function.

18. The method of claim 10, wherein the mapping transformation function is generated using a mean position of each of the reference nodes.

19. The method of claim 10, wherein the mapping transformation function is generated at a specific cardiac phase.

20. The method of claim 10 wherein each of the plurality of reference nodes is tracked through ultrasound means.

21. A method for determining a motion compensated node location in a three-dimensional coordinate system associated with a node disposed on a first medical device within a body, the method comprising:

determining a plurality of reference locations in said coordinate system corresponding to a plurality of reference nodes disposed on a second medical device and a third medical device;

determining a mapping transformation function configured to transform the reference locations associated with each of the plurality of reference nodes to be defined as corresponding constant locations over time in said coordinate system such that the reference locations are an input to the mapping transformation function and the corresponding constant locations are an output to the mapping transformation function to thereby define a static model of the second medical device, wherein the transformed reference locations of the corresponding constant locations define a static position of the second medical device; and determining the motion compensated node location associated with the node disposed on the first medical by applying the determined mapping transformation function to a raw node location in said coordinate system associated with the node, wherein the node disposed on the first medical device comprises a first node and wherein the first medical device further comprises a second node, the first node and the second node selected from at least one of an electromagnetic field node and a magnetic position node, wherein applying the determined mapping transformation to the raw node location includes:

applying the determined mapping transformation function to a first raw node location associated with the first node to determine a first motion compensated node location associated with the first node; and applying the determined mapping transformation function to a second raw node location associated with the second node to determine a second motion compensated node location associated with the second node.

* * * * *